(12) United States Patent
Pokorski et al.

(10) Patent No.: US 8,697,898 B2
(45) Date of Patent: Apr. 15, 2014

(54) MEDICAL APPLICATION OF LIPID DERIVATIVES OF DOPAMINE AND THE METHODS OF THEIR PRODUCTION

(75) Inventors: Mieczyslaw Pokorski, Warsaw (PL); Dominika Zajac, Warsaw (PL); Zbigniew Czarnocki, Warsaw (PL); Piotr Roszkowski, Warsaw (PL)

(73) Assignees: Instytut Medycyny Doswiadczalnej i Klinicznej im. M. Mossakowskiego PAN, Warsaw (PL); Uniwersytet Warszawski, Warsaw (PL)

( * ) Notice: Subject to any disclaimer, the term of this patent is extended or adjusted under 35 U.S.C. 154(b) by 0 days.

(21) Appl. No.: 13/303,935

(22) Filed: Nov. 23, 2011

(65) Prior Publication Data

US 2013/0131361 A1   May 23, 2013

(51) Int. Cl.
*C07C 231/00* (2006.01)
*C07C 233/00* (2006.01)

(52) U.S. Cl.
USPC .......................................................... 554/65

(58) Field of Classification Search
USPC .......................................................... 554/65
See application file for complete search history.

(56) References Cited

FOREIGN PATENT DOCUMENTS

| EP | 2324824 A2 | * | 5/2011 |
| EP | 2324824 | | 6/2011 |

OTHER PUBLICATIONS

Almasi et al. Life Science 2008, vol. 82, p. 644-651, "Actions of 3Omethyl-N-oleydopamine, 4-methyl-N-oleoyldopamine and N-oleoylethanolamide on the rat TRPV1 receptor in vitro and in vivo."
Konieczny et al. International Journal of Immunopathology and Pharmacology 2009, vol. 22, No. 1, p. 21-28, "N-Oleoyl-Dopamine Decreases Muscle Rigidity Induced by Reserpine in Rats."
Przegalinski et al. International Journal of Immunopathology and Pharmacology 2006, vol. 19, No. 3, p. 451-460, "N-Oleoyl-Dopamine Increases Locomotor Activity in the Rat."
Zajac et al. Journal of Physiology and Pharmacology 2006, vol. 57, Supp.4, p. 403-408, "Membrane Association of N-Oleoyl-Dopamine in Rat Brain."

* cited by examiner

*Primary Examiner* — Deborah D Carr
(74) *Attorney, Agent, or Firm* — Brooks Kushman P.C.

(57) ABSTRACT

A medical application of N-oleoyl-dopamine and 3'-O-methyl-N-oleoyl-dopamine for the production of a medication for treatment or prophylaxis of disturbances or states due to deficiency of dopamine, preferably chosen from the group covering oxygen deficiencies (hypoxia) in anesthetized and awake mammals, breathing with atmospheric oxygen (normoxia), for the respiratory responses to hypoxia in mammals, lack of dopamine binding to the membrane system in the mammalian brain, disturbances in metabolic pathways of dopamine metabolism, states of dopamine deficiencies provoked by morbid or genetic factors as well as under condition connected to the physiological process of aging of the organism, through the systemic introduction of the compound to the mammalian organism. A method of production of 3'-O-methyl-N-oleoyl-dopamine in vitro is also disclosed.

7 Claims, 2 Drawing Sheets

Structure 1

Structure 2

MEDICAL APPLICATION OF LIPID DERIVATIVES OF DOPAMINE AND THE METHODS OF THEIR PRODUCTION

CROSS-REFERENCE TO RELATED APPLICATIONS

This application is related to European application EP 10191670.8, filed Nov. 18, 2010, and Polish application PL38962109, filed Nov. 19, 2009, which are incorporated in their entirety by reference herein.

TECHNICAL FIELD

Application of the lipid derivatives of dopamine for use in augmentation of brain dopamine level.

BACKGROUND

Both N-oleoyl-dopamine and 3'-O-methyl-N-oleoyl-dopamine are until now the very poorly described substances. In the literature, their agonistic action towards TRPV1 vanilloid receptors is mentioned.

Additionally, the presence of N-oleoyl-dopamine in mammalian brains as well as its ability to penetrate into the brain after injection into the carotid artery which leads blood to the brain have been proved.

It has been discovered that N-oleoyl-dopamine is a highly stable compound under in vitro conditions and that it diminishes muscle rigidity in a rat model of Parkinson's disease. N-oleoyl-dopamine also increases the locomotive activity in the rat.

Until now, neither of the above mentioned derivatives of dopamine has been used to modify the body response to a hypoxic stimulus and to achieve an augmentation of the dopamine level in physiological and pathological states of its deficiency.

SUMMARY

The present embodiment comprises of novel applications of the lipid derivatives of dopamine N-oleoyl-dopamine, with the structure presented in Structure 1, and 3'-O-methyl-N-oleoyl-dopamine, with the structure presented in Structure 2, as oleic derivatives of dopamine, especially in the context of the response to hypoxic stimuli and of the augmentation of the brain dopamine level under physiological and pathological conditions in case of its deficiencies. The method of production of 3'-O-methyl-N-oleoyl-dopamine, presented in Structure 2, is part of the present embodiment as well.

DETAILED DESCRIPTION

Figure 1:
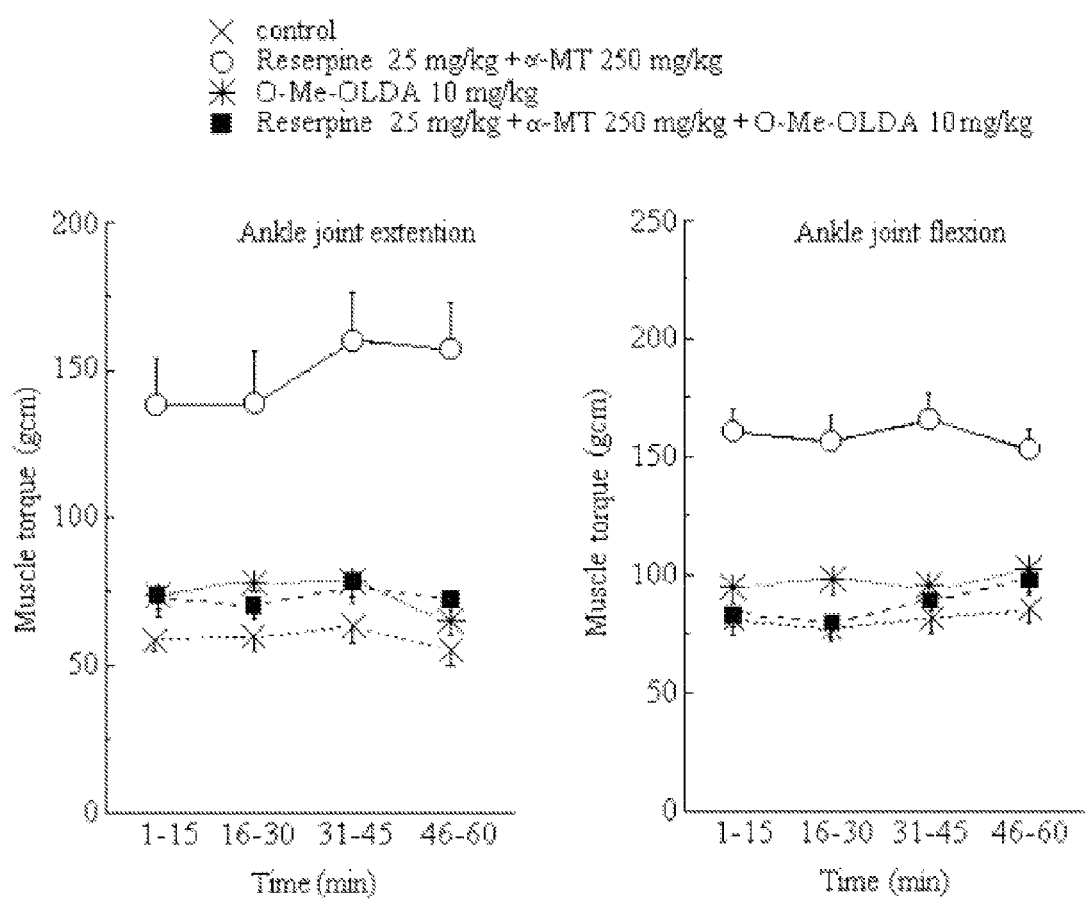
FIG. 1 illustrates changes in muscle torque in the rat model of Parkinson's disease after 3'-O-methyl-N-oleoyl-dopamine.
Figure 2:
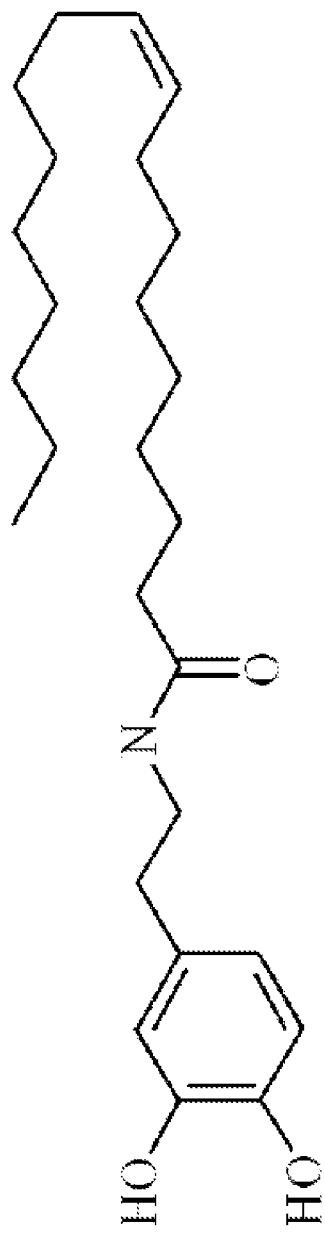
FIG. 2 illustrates chemical structure 1.
Figure 3:
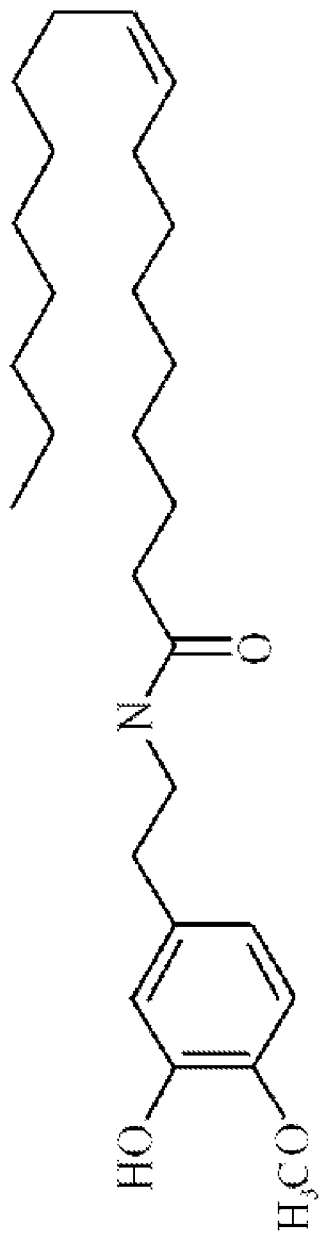
FIG. 3 illustrates chemical structure 2.

Medical applications of N-oleoyl-dopamine for production of a medication for treatment or prophylaxis of disturbances or states due to deficiencies in dopamine, preferably chosen from the group covering also oxygen deficiencies (hypoxia) in the anesthetized and awake mammal, breathing with atmospheric oxygen (normoxia), respiratory responses to hypoxia in mammals, lack of dopamine binding to the membrane system of the mammalian brain, disturbances in the metabolic pathways of dopamine metabolism, states of dopamine deficiencies provoked by morbid or genetic factors as well as under conditions connected with the physiological process of aging of the organism, through the systemic introduction of the compound to the mammalian organism.

Morbid conditions with disturbances in respiration are understood as all neurodegenerative diseases connected with disturbances in dopaminergic transduction, particularly Parkinson's disease and the like, and genetic deficiencies in dopamine receptors or dopamine synthesizing systems, that is, all conditions under which there is not enough dopamine or it is not properly used in the body. Simultaneously, any of these changes can be in connection with the central and peripheral nervous system as well as with muscles, e.g. respiratory muscles. One of the diseases with malfunctions of dopamine activity is ADHD (Attention Deficit Hyperactivity Disorder).

Particularly, N-oleoyl-dopamine is used for:

a) Modulation of respiratory responses to oxygen deficiency (hypoxia) in the anesthetized rat and the involvement of the dopaminergic system into this response.

b) Influence on respiration under normoxic conditions (breathing with atmospheric oxygen) and on the respiratory response to hypoxia in the awake rat and the involvement of the dopaminergic system into this response.

c) Binding of N-oleoyl-dopamine to the brain membrane system after introduction to the organism (systemic administration).

d) Participation of dopaminergic pathways in the metabolism.

e) Application as a means for supplementation in dopamine deficiencies under physiological, connected to ageing, and pathological, e.g. Parkinson's disease like conditions.

Medical applications of 3'-O-methyl-N-oleoyl-dopamine for the production of a medication for treatment or prophylaxis of disturbances or states due to deficiencies of dopamine, preferably chosen from the group covering oxygen deficiencies (hypoxia) in the anesthetized and awake mammal, breathing with atmospheric oxygen (normoxia), for respiratory responses to hypoxia in mammals, lack of dopamine binding to the membrane system of the mammalian brain, for the disturbances in metabolic pathways of dopamine metabolism, the states of dopamine deficiencies provoked by morbid or genetic factors as well as under conditions connected with the physiological process of aging of the organism, through the systemic introduction of the compound to the mammalian organism.

Morbid conditions with disturbances in respiration are understood as all neurodegenerative diseases connected to the disturbances in dopaminergic transduction, preferably Parkinson's disease and related as well as genetic deficiencies in dopamine receptors or dopamine synthesizing systems, that is, all conditions under which there is not enough dopamine or it is not properly used. Simultaneously, any of these changes can be in connection to the central and peripheral nervous system as well as with muscles, e.g., respiratory muscles. One of diseases with malfunctions of dopamine activity is ADHD (Attention Deficit Hyperactivity Disorder).

Particularly, 3'-O-methyl-N-oleoyl-dopamine is used for:

a) Influence on respiration under normoxic and hypoxic conditions in the awake rat.

b) In vivo influence of 3'-O-methyl-N-oleoyl-dopamine on muscular symptoms of Parkinson's disease in the rat model.

c) Application as a means for supplementation in dopamine deficiencies under physiological, connected to aging, and pathological, e.g., Parkinson's disease-like conditions.

Another action of both N-oleoyl-dopamine and 3'-O-methyl-N-oleoyl-dopamine is supposed to be alleviation of symptoms of the Attention Deficiency Hyperactivity Disorder (ADHD). This disease is in connection to disturbances in the dopaminergic system manifested by insufficient binding of dopamine to the effector system. The administration of both N-oleoyl-dopamine and 3'-O-methyl-N-oleoyl-dopamine as a vector of dopamine to the cell membranes of the nervous system showing high systemic stability would increase the local concentration of dopamine directly in the cell membranes and in consequence prevent the insufficient binding of endogenous dopamine with effector systems. A measurable effect would be the restoration of the desired dopamine level and improvement of action of the dopaminergic system.

Another subject of embodiment is the method of production of 3'-O-methyl-N-oleoyl-dopamine.

The method of production of 3'-O-methyl-N-oleoyl-dopamine in vitro comprises, according to the present embodiment, of the reaction of 3-O-methyl-dopamine hydrochloride with oleic acid in the presence of, preferably, BOP (Benzotriazole-1-yl-oxy-tris-(dimethylamino)-phosphonium hexafluorophosphate), DCC (N,N'-dicyclohexylcarbodiimide), DMAP (4-Dimethylaminopyridine) and THF (tetrahydrofuran), $CH_2Cl_2$ (dichloromethane), $CHCl_3$ (chloroform), toluene, diethyl ether. The reaction mixture is cooled to a temperature of 0-10° C., a solution of trietanolamine is added under continuous stirring and 3'-O-methyl-N-oleoyl-dopamine is precipitated and purified by a known method.

A variant method of production of 3'-O-methyl-N-oleoyl-dopamine comprises, according to the present embodiment, the action of methylation of N-oleoyl-dopamine by the catechol-O-methyltransferase (COMT) in the presence of S-adenosyl-L-methionine (SAM) and magnesium ions in phosphate buffered saline (PBS) solution buffered to pH of 7.0-8.0 at temperature of 25-45° C. Afterwards, 3'-O-methyl-N-oleoyl-dopamine is precipitated and purified by a known method.

Examples of execution of the present embodiment are shown below.

DESCRIPTION OF EMBODIMENTS

Example I

Influence of N-oleoyl-dopamine on the respiratory response to oxygen deficiency (hypoxia) in the anesthetized rat and the involvement of the dopaminergic system into this response.

N-oleoyl-dopamine decreases the stimulatory respiratory response to the hypoxic stimulus in both, the first stimulatory and the second inhibitory, phases of the response. This response appears mainly via the increased frequency of respiration, which is generated by the respiratory chemoreceptors in the sensory organs called the carotid bodies. Additionally, in the inhibitory action of N-oleoyl-dopamine, the dopaminergic system is involved. This was asserted by the suppression of the effect of N-oleoyl-dopamine after blockade of dopamine receptors.

The study was performed in anesthetized, paralyzed and artificially ventilated Wistar rats. During the experiments, the integrated activity of the phrenic nerve was recorded. This activity reflects the frequency and tidal volume; their product represents the index of minute lung ventilation. The experimental protocol consisted of control recordings for two levels of the hypoxic stimulus: 14% and 11% $O_2$ in $N_2$. Afterwards, N-oleoyl-dopamine in a dose of 20 mg/kg was given and the recordings were repeated. Additionally, experiments with two dopamine receptor antagonists were performed: first, with the penetrating through the blood-brain barrier D2 dopamine receptor antagonist haloperidol and second, with the non-penetrating through the blood-brain-barrier domperidone. In these studies, after the control recordings, haloperidol (in a dose of 3 mg/kg) or domperidone (in a dose of 0.3 mg/kg) were administered and the recordings repeated. Then, N-oleoyl-dopamine was given and the recordings were repeated.

N-oleoyl-dopamine reduced the respiratory response to hypoxia at both levels of the stimulus and in both phases of the response: stimulatory and inhibitory. The peak respiratory response was, in relation to the starting-point values, diminished from 40±11% (control) to 18±10% (N-oleoyl-dopamine) and from 56±9% (control) to 38±9% (N-oleoyl-dopamine) for 14 and 11% hypoxia, respectively.

In separate experiments, where haloperidol alone was given, it decreased the peak respiratory response from 28±6% to 18±3% and from 62±10% to 22±5% for 14% and 11% hypoxia, respectively. Haloperidol also diminished the respiration in the second inhibitory phase. A subsequent administration of N-oleoyl-dopamine did not restore the respiratory response in the first stimulatory phase, but still diminished it in the second inhibitory phase. An identical situation occurred in case of administration of the selectively peripheral dopamine receptor antagonist domperidone, which abolished the respiratory response to hypoxia in the first stimulatory phase from 25±4% (control) to 21±5% (domperidone) and from 45±5% (control) to 26±5% (domperidone) for 14% and 11% hypoxia, respectively. Further administration of N-oleoyl-dopamine did not change the response to hypoxia in the stimulatory phase, but still diminished the respiration in the inhibitory phase. All changes occurred at the level of frequency and minute ventilation.

As for the first stimulatory phase of the respiratory response to hypoxia, peripheral chemoreceptors of the carotid bodies are responsible and their main neurotransmitter is dopamine, the above mentioned results lead to the conclusion that N-oleoyl-dopamine influences the respiratory response to hypoxia in the anesthetized rat involving the peripheral dopaminergic system. Additionally, it decreases the respiratory response to hypoxia also at the level of the central nervous system involving other non-dopaminergic neurotransmitter systems.

Example II

Influence of N-oleoyl-dopamine on respiration with atmospheric oxygen (normoxia) and the respiratory response to oxygen deficiency (hypoxia) in the awake rat and the involvement of the dopaminergic system into this response.

N-oleoyl-dopamine reduces the pulmonary ventilation during breathing with atmospheric oxygen and the respiratory response to oxygen deficiency (hypoxic stimulus) in the non-anesthetized, awake rat in both stimulatory and inhibitory phases. These decreases occur mainly at the level of the frequency of breathing. In the inhibitory action of N-oleoyl-dopamine on respiration during hypoxia, the dopaminergic system is involved as blockade of dopamine receptors abolishes the action of N-oleoyl-dopamine.

The study was performed in awake Wistar rats in a computerized plethysmographic chamber for small rodents. Respiratory frequency, tidal volume and pulmonary ventilation were measured. The experimental protocol included recordings in normoxia (breathing with atmospheric air), two levels of hypoxic stimulus (8% and 12% $O_2$ in $N_2$), intraperitoneal (i.p.) administration of N-oleoyl-dopamine (in a dose of 40 mg/kg) and repeated recordings for both normoxic and hypoxic states. Additionally, further experiments with the dopamine receptor antagonist haloperidol (in a dose of 0.9 mg/kg, i.p.) were performed. In those experiments, haloperidol was administered prior to N-oleoyl-dopamine and the recordings according the above-mentioned protocol were repeated.

N-oleoyl-dopamine decreased resting ventilation during breathing with atmospheric oxygen by 33%. The observed reduction occurred mainly via the decrease in respiratory frequency which was diminished by 23%.

N-oleoyl-dopamine significantly decreased the respiratory response at both levels of the hypoxic stimulus in both phases of the respiratory response—the stimulatory and inhibitory ones. The peak respiratory response decreased after administration of N-oleoyl-dopamine from 1335.5±99.1 to 856.6±73.7 ml/min/kg body weight in case of 12% hypoxia and from 2279.0±237.8 to 1338.3±49.5 ml/min/kg body weight in case of 8% hypoxia, which corresponds to the 36% and 41% reductions.

In case of blockade of the dopaminergic system with haloperidol, only a slight reduction of the peak respiratory response after N-oleoyl-dopamine administration was observed.

Minute lung ventilation decreased from 1605.4±61.2 (prior to the administration of haloperidol and N-oleoyl-dopamine) to 1484.0±92.3 ml/min/kg body weight (after administration of haloperidol and N-oleoyl-dopamine) for 12% hypoxia and from 2007.8±62.4 (prior to administration of haloperidol and N-oleoyl-dopamine) to 1947.3±66.5 ml/min/kg body weight (after administration of haloperidol and N-oleoyl-dopamine) for 8% hypoxia.

As for the first stimulatory phase of the respiratory response to hypoxia, peripheral chemoreceptors are responsible and their main neurotransmitter is dopamine. Thus, the above mentioned results lead to the conclusion that N-oleoyl-dopamine influences the respiratory response to hypoxia in the awake rat involving the dopaminergic system.

Example III

Binding of N-Oleoyl-Dopamine to the Rat Brain Membrane System after Intraperitoneal (Systemic) Administration N-oleoyl-dopamine penetrates after intraperitoneal administration into the brain tissue of the rat where it binds to the membrane system staying unchanged for at least 24 hours.

N-oleoyl-dopamine was administered to Wistar rats at a dose of 20 mg/kg. After 1, 2, 3 or 24 hours the rat was sacrificed and the brain was resected. From the tissue, the whole lipid fraction, containing all lipids of the brain and the membrane fraction of the rat brain were obtained. Total lipids were obtained by homogenization of the brain in a mixture of chloroform and methanol 2:1 followed by an extraction of the water-soluble fractions and evaporation of the solvent. The membrane phase was obtained according to Xu et al. (Xu, 1998) and extracted with chloroform to obtain membrane lipids. All obtained samples were analyzed by the thin layer chromatography TLC on silica gel plates 60 using a mixture of chloroform and methanol 95:5 as the mobile phase and N-oleoyl-dopamine as the standard. The Retention Factor (Rf) for the N-oleoyl-dopamine standard was equal to 0.24-0.26. At the same level (the same Rf=0.24-0.29) there were bands corresponding to N-oleoyl-dopamine in the biological samples, that is after systemic N-oleoyl-dopamine injection, but not in the control samples obtained with no N-oleoyl-dopamine injection.

The results of the above described experiments indicate that N-oleoyl-dopamine penetrates into the membrane system of the rat brain after systemic administration and exhibits a high stability in this system in vivo.

Example IV

Participation of Dopaminergic Metabolic Pathways in the Metabolism of N-oleoyl-dopamine N-oleoyl-dopamine undergoes the O-methylation by the catechol-O-methyltransferase, one of the enzymes taking part in the dopaminergic metabolic pathway.

N-oleoyl-dopamine underwent the reaction of methylation with the catechol-O-methyltransferase in PBS buffer pH=8 with 10 mM magnesium ions as the co-factor and S-adenosyl-L-methionine as the donor of methyl groups. The reaction was conducted for one hour at 37° C. After the termination of the reaction, the reaction mixture was extracted with chloroform to obtain an organic and an aqueous phase. Both phases were analyzed using UV/VIS spectrophotometry and high performance liquid chromatography with mass detection (HPLC/MS). It was shown that the organic phase contained both N-oleoyl-dopamine and 3'-O-methyl-N-oleoyl-dopamine (the substrate and the product of the reaction, respectively), and the aqueous phase S-adenosyl-L-methionine and its demethylated derivative, S-adenosyl-L-homocystein (the substrate and the product of the reaction, respectively). The obtained results were additionally confirmed with the mass spectrometry (MS).

The results of the above described experiments indicate that N-oleoyl-dopamine undergoes the O-methylation by the catechol-O-methyltransferase to 3'-O-methyl-N-oleoyl-dopamine in vitro, which leads to the conclusion that 3'-O-methyl-N-oleoyl-dopamine might be included into the metabolic pathways of dopamine.

Example V

Synthesis of 3'-O-methyl-N-oleoyl-dopamine (Method I)

0.462 g (2.27 mmol) of 3-O-methyldopamine hydrochloride, 0.641 g (2.27 mmol) of oleic acid, 1.000 g (2.27 mmol) of BOP (Benzotriazol-1-yloxytris(dimethylamino)-phosphonium hexafluorophosphate) and 20 ml of THF were introduced into a flask. The reaction mixture was cooled down to a temperature of 0-5° C. and 0.949 ml (6.810 mmol) of triethanolamine in 4 ml THF were added drop-wise within 15 min and the reaction mixture was continuously stirred for 15 hours at room temperature. After evaporating the solvent, 100 ml of diethyl ether were added and the ether phase was washed three times with 30 ml of a 4% HCl solution, two times with 30 ml of a saturated $NaHCO_3$ solution and two times with a saturated NaCl solution. After drying over anhydrous $MgSO_4$ and removal of the solvent, the crude product was purified by crystallization from diethyl ether/hexane. 0.90 g (2.09 mmol) of the amide in the form of a white solid was obtained giving the reaction yield of 92%.

Melting point: 78-79° C.

NMR: $^1$H NMR: d 6.80 (d, J=7.5 Hz, 1H-5'), 6.69-6.65 (m, 2H-2', 6'), 5.70 (s, 1H—NH), 5.50 (s, 1H—OH), 5.38-5.30 (m, 2H-9.10), 3.87 (s, 3H—OCH$_3$), 3.48 (q, J=6.0 Hz, 2H-1"), 2.74 (t, J=7.0 Hz, 2H-2"), 2.12 (t, J=8.0 Hz, 2H-2), 2.02-1.98 (m, 4H-8, 11), 1.60-1.57 (m, 2H-3), 1.32-1.26 (m, 20H-4, 5, 6, 7, 12, 13, 14, 15, 16, 17), 0.88 (t, J=7.0 Hz, 3H-18).

$^{13}$C NMR: d 173.17, 146.67, 144.29, 130.67, 130.01, 129.74, 121.31, 114.42, 111.16, 55.89, 40.69, 36.87, 35.39, 31.91, 29.77, 29.72, 29.53, 29.33, 29.28, 29.27, 29.14, 27.23, 27.18, 25.78, 22.69, 14.13; Mass spectrometry: m/z=432.6 [M+H]$^+$, 454.6 [M+Na]$^+$;

Example VI

The synthesis of 3'-O-methyl-N-oleoyl-dopamine (Method II)

The reaction was conducted in PBS buffer pH=8 enriched with magnesium ions at a concentration of 10 mmol/l. The reaction mixture consisted of 0.5 mg catechol-O-methyl-transeraze (activity 1.107 µmol of substrate per hour) in 1% albumin solution, 0.865 mg (1.107 µmol) S-adenosyl-L-methionine (SAM) and 0.463 mg (1.107 µmol) N-oleoyl-dopamine and was stirred for one hour at 37° C. Afterwards, proteins were precipitated with trichloracetic acid, the solution was centrifuged at 1200×g for 10 min and the pellet discarded. The supernatant was extracted four times with 0.25 ml of chloroform giving the organic phase. The sample was evaporated under nitrogen and 3'-O-methyl-N-oleoyl-dopamine was obtained.

Example VII

Influence of 3'-O-methyl-N-oleoyl-dopamine on Respiration During Normoxia and Hypoxia in the Awake Rat 3'-O-methyl-N-oleoyl-dopamine decreased pulmonary ventilation during respiration with atmospheric oxygen (normoxia) and the respiratory response to a hypoxic stimulus (oxygen deficiency) in the awake rat.

The study was performed in awake Wistar rats in a computerized plethysmographic chamber for small rodents. Respiratory frequency, tidal volume and pulmonary ventilation were measured. The experimental protocol included recordings for normoxia (breathing with atmospheric air), for two levels of hypoxic stimulus (8% and 12% O$_2$ in N$_2$), intraperitoneal (i.p.) administration of 3'-O-methyl-N-oleoyl-dopamine (in a dose of 40 mg/kg), and then repeated recordings for both normoxic and hypoxic states.

3'-O-methyl-N-oleoyl-dopamine decreased resting ventilation during breathing with atmospheric oxygen from 1012.2±163.8 (prior to administration) to 779.7±148.7 ml/min/kg body weight (after administration of 3'-O-methyl-N-oleoyl-dopamine), which corresponds to a 23% fall. 3'-O-methyl-N-oleoyl-dopamine also decreased the respiratory response at both levels of hypoxia in both stimulatory and inhibitory phase. After administration of 3'-O-methyl-N-oleoyl-dopamine, the peak respiratory response decreased in case of 8% hypoxia from 2382±277 (prior to administration) to 1939±255 ml/min/kg body weight (after administration of 3'-O-methyl-N-oleoyl-dopamine), which is equal to a 19% decline. This decrease occurred mainly at the level of the frequency component of the minute ventilation.

The above-described observations lead to a conclusion that 3'-O-methyl-N-oleoyl-dopamine decreases minute ventilation in the awake rat both during normoxia and under a hypoxic stimulus.

Example VIII

Action of 3'-O-methyl-N-oleoyl-dopamine In Vivo

3'-O-methyl-N-oleoyl-dopamine abolishes muscle rigidity in an animal model of Parkinson's disease.

Symptoms of the Parkinson's disease, particularly muscle rigidity during flexion and extension movements in the ankle joint, were induced with reserpine (2.5 mg/kg, i.p.) and a-methyl-tyrosine (α-MT, 250 mg/kg, i.p.) administered at a 16-h interval. Afterwards, 3'-O-methyl-N-oleoyl-dopamine (O-Me-OLDA) was administered at a dose of 10 mg/kg and the muscular tone was measured using electromyographic (EMG) techniques. The control groups consisted of a) only vehiculum-treated animals in which no symptoms of Parkinson's disease were induced (control), b) animals who received only 3'-O-methyl-N-oleoyl-dopamine (O-Me-OLDA) and c) animals in which symptoms of Parkinson's disease were induced (reserpine+α-MT), but no other treatment was introduced.

It was found that the mixture of resepine and a-methyl-tyrosine increases the muscle tone during flexion and extension movements of the ankle joint (reserpine+α-MT). 3'-O-methyl-N-oleoyl-dopamine alone did not change the muscle tone in comparison to control recordings (O-Me-OLDA, control). Administration of 3'-O-methyl-N-oleoyl-dopamine in rats showing symptoms of Parkinson's disease abolished muscle rigidity in this model (reserpine+α-MT+O-Me-OLDA). The observed effect remained unchanged during the whole experimental period. The obtained results are presented on FIG. 1.

Example IX

Possibility of application of N-oleoyl-dopamine and 3'-O-methyl-N-oleoyl-dopamine as a means for dopamine supplementation in dopamine deficiencies under physiological, connected to aging, and pathological conditions (e.g. in a rat model of Parkinson's disease and the ADHD (Attention Deficiency Hyperactivity Disorder).

In connection to the observed penetration of N-oleoyl-dopamine and 3'-O-methyl-N-oleoyl-dopamine into the nervous tissue after systemic administration and their proven dopamine-like action, both N-oleoyl-dopamine and 3'-O-methyl-N-oleoyl-dopamine are carriers of the information connected to the molecule of dopamine, especially when it penetrates through biological barriers. Additionally, as these compounds interact with the dopaminergic system, both at the peripheral and central level, they abolish the consequences of dopamine deficiencies in the nervous tissue.

Deficiencies of dopamine in the nervous system occur in the process of aging as well as in numerous neurodegenerative diseases of the brain, of which a leading example is Parkinson's disease. N-oleoyl-dopamine and 3'-O-methyl-N-oleoyl-dopamine, as substances interacting with the dopaminergic system of the nervous tissue, diminish the consequences of these deficiencies and can, in this way, alleviate both the ailments connected to aging of the organism and the consequences of neurodegenerative brain diseases. Due to the ease of penetration of these derivatives of dopamine through biological barriers, and the simultaneous slight toxicity, they are a promising alternative to substances used so far in these diseases. In connection to their parallel interaction with the vanilloid system, which is involved into the pain transmission, the described herein molecules constitute potential analgesic drugs. The combination of the dopamine-like action, the alleviation of ailments connected to aging and neurodegenerative diseases, and the analgesic and warming properties (which is proper to vanilloids) seems to be extremely favorable in regard to a frequent co-existence of these symptoms.

INDUSTRIAL APPLICABILITY

3'-O-methyl-N-oleoyl-dopamie has a clear, reducing action on muscle tone and muscle rigidity, therefore a myorelaxant action. This was found in a model of elevated muscle rigidity, experimentally induced in rats by injections of reserpine. This method is a pharmacological tool for modeling the typical, dopamine-deficiency-related brain symptoms of Parkinson's disease in rats. 3'-O-methyl-N-oleoyl-dopamine significantly diminished or abolished muscle rigidity induced by reserpine. Strong myorelaxant effects of 3'-O-methyl-N-oleoyl-dopamine are observed already at lower doses than in case of N-oleoyl-dopamine. Examples of such interaction of 3'-O-methyl-N-oleoyl-dopamine are shown in FIG. 1, where it is presented that 3'-O-methyl-N-oleoyl-dopamine, already at a dose of 10 mg/kg, decreases nearly down to the control level, the three-fold elevated level of muscle tone by reserpine, as analyzed by the generation of the force needed for flexion and extension of the ankle joint.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method comprising:
  introducing a lipid derivative of dopamine to a mammal for treatment or prophylaxis of disturbances or states due to deficiency of dopamine, the lipid derivative of dopamine being of N-oleoyl-dopamine.

2. The method of claim 1 wherein the disturbances or states due to deficiency of dopamine are elected from the group consisting of oxygen deficiencies (hypoxia) in anesthetized and awake mammals, breathing with atmospheric oxygen (normoxia), hypoxia, lack of dopamine binding to a membrane system in a mammalian brain, disturbances in metabolic pathways of dopamine metabolism, states of dopamine deficiencies provoked by morbid or genetic factors, and conditions connected to a physiological process of aging.

3. A method comprising:
  introducing a lipid derivative of dopamine to a mammal for treatment or prophylaxis of disturbances or states due to deficiency of dopamine, the lipid derivative of dopamine being 3'-O-methyl-N-oleoyl-dopamine.

4. The method of claim 3 wherein the disturbances or states due to deficiency of dopamine are elected from the group consisting of oxygen deficiencies (hypoxia) in anesthetized and awake mammals, breathing with atmospheric oxygen (normoxia), hypoxia, lack of dopamine binding to a membrane system in a mammalian brain, disturbances in metabolic pathways of dopamine metabolism, states of dopamine deficiencies provoked by morbid or genetic factors, and conditions connected to a physiological process of aging.

5. A method of forming 3'-O-methyl-N-oleoyl-dopamine in vitro, the method comprising:
  reacting 3-O-methyl-dopamine hydrochloride with oleic acid to form a reaction mixture;
  cooling the reaction mixture to a temperature of 0-10° C.;
  adding a solution of triethanolamine to the reaction mixture under continuous stirring;
  precipitating 3'-O-methyl-N-oleoyl-dopamine from the reaction mixture; and
  purifying the 3'-O-methyl-N-oleoyl-dopamine.

6. The method of claim 5 wherein 3-O-methyl-dopamine hydrochloride is reacted with oleic acid in the presence of benzotriazole-1-yl-oxy-tris-(dimethylamino)-phosphonium hexafluorophosphate), N,N'-dicyclohexylcarbodiimide, 4-dimethylaminopyridine, tetrahydrofuran), dichloromethane, chloroform, toluene, and diethyl ether.

7. A method of forming 3'-O-methyl-N-oleoyl-dop amine comprising: methylating N-oleoyl-dopamine with catechol-O-methyltransferase (COMT) in the presence of S-adenosyl-L-methionine (SAM) and magnesium ions in a phosphate buffered saline (PBS) solution buffered to pH of 7.0-8.0 at temperature of 25-45° C.; and
  precipitating 3'-O-methyl-N-oleoyl-dopamine; and
  purifying the 3'-O-methyl-N-oleoyl-dopamine.

* * * * *